United States Patent
Thibault et al.

(10) Patent No.: US 6,969,375 B2
(45) Date of Patent: Nov. 29, 2005

(54) SEALED CONNECTION DEVICE FOR MEDICAL USE OF THE LUER LOCK TYPE AND SYRINGE INCORPORATING SUCH A DEVICE

(75) Inventors: Jean-Claude Thibault, Saint Egreve (FR); Hubert Jansen, Jarrie (FR); Jean-Pierre Grimard, VIF (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/296,429

(22) PCT Filed: May 23, 2001

(86) PCT No.: PCT/FR01/01615

§ 371 (c)(1), (2), (4) Date: Apr. 21, 2003

(87) PCT Pub. No.: WO01/91839

PCT Pub. Date: Dec. 6, 2001

(65) Prior Publication Data

US 2003/0163093 A1 Aug. 28, 2003

(30) Foreign Application Priority Data

May 26, 2000 (FR) ............................................. 00 06793

(51) Int. Cl.[7] .............................................. A61M 5/31
(52) U.S. Cl. ...................................................... 604/241
(58) Field of Search ................................. 604/240–245, 604/110, 198, 163, 263, 164.07, 181, 533–535, 187

(56) References Cited

U.S. PATENT DOCUMENTS

| 4,589,871 A | * | 5/1986 | Imbert ......................... 604/240 |
| 4,927,417 A | * | 5/1990 | Moncada et al. ........... 604/198 |

FOREIGN PATENT DOCUMENTS

DE 19956243 A1 * 5/2000 ............ A61M/5/32

* cited by examiner

Primary Examiner—Nicholas D. Lucchesi
Assistant Examiner—Matthew F DeSanto
(74) Attorney, Agent, or Firm—David M. Fortunato

(57) ABSTRACT

Luer lock type connection device for medical use having a nozzle in which an axial internal passage is formed. The nozzle includes a bearing connection surface and a proximal annular retention zone. The connection device also has a flange forming an axial open seat having a wall that includes a distal part with internal screw thread, and a transverse proximal part in which a central proximal retention opening is formed, and whose diameter is matched to that of the proximal annular zone of the nozzle. The proximal annular retention zone of the nozzle and/or the central proximal retention opening of the flange include a circular band or cord covered or treated with a roughening agent.

4 Claims, 2 Drawing Sheets

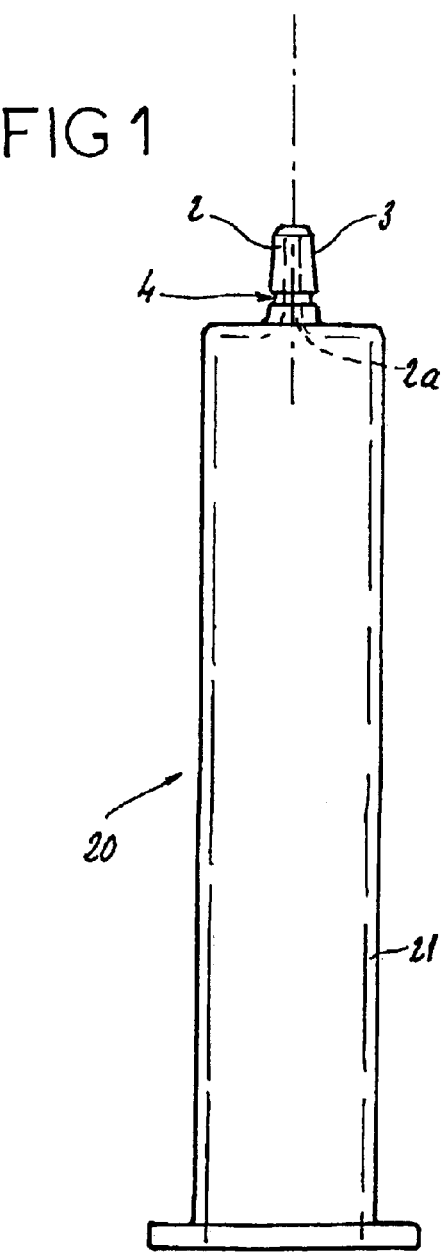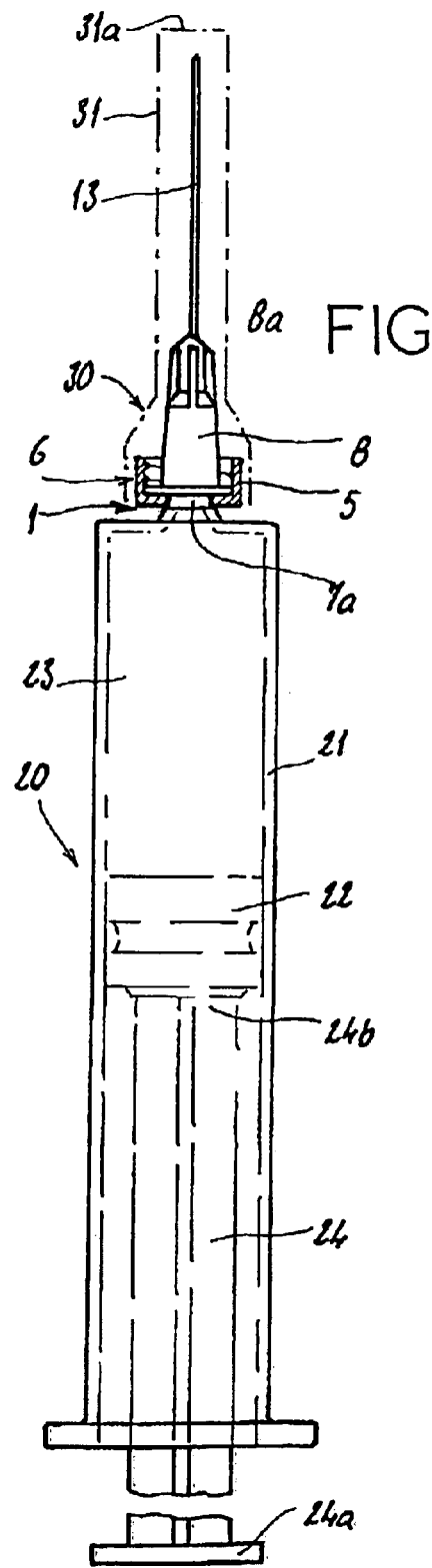

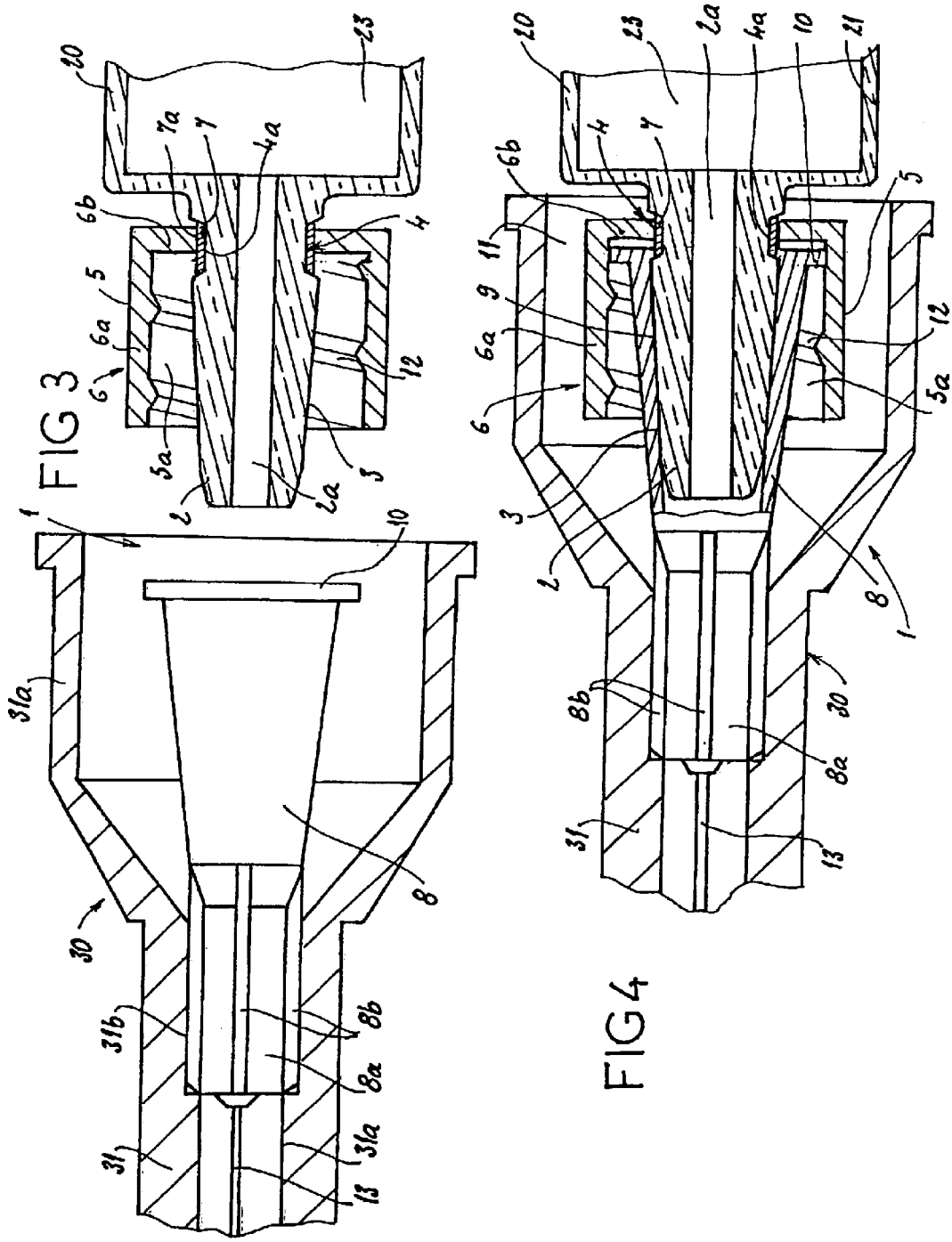

SEALED CONNECTION DEVICE FOR MEDICAL USE OF THE LUER LOCK TYPE AND SYRINGE INCORPORATING SUCH A DEVICE

The present invention pertains to connection devices for medical use, and more particularly to devices of the Luer-lock type.

The device that is the object of the present invention comprises in general:

a) An adapter provided with an axial passage; this adapter includes a juncture seat, for example an external distal seat fitted by friction, e.g., of a frustoconical shape, and a proximal annular retention zone, consisting of a flat-bottomed groove for example;

b) An attached collar, providing an axial and distal open housing, the wall of which comprises a distal part with an internal threading and a proximal part in which a central proximal opening is provided; the diameter of this opening is adjusted to that of the proximal annular zone of the adapter; the collar is attached or connected in a translational and/or rotational manner to the adapter, by insertion between the proximal annular retention zone of the adapter on the one hand and the proximal central retention zone on the other;

c) A connection device comprising another additional junction seat, e.g., an internal friction-fitted seat, adjusted to fit the junction seat of the adapter; this device has at least one proximal and transverse external flange, forming a thread adjusted to the internal threading of the collar, with an axial passage in fluid communication with the interior of the cap.

Such a device is more particularly associated with a syringe, which also traditionally comprises a hollow body forming a chamber for a liquid to be ejected or drawn into the said syringe, a sealant joint provided on the inside of the body to delimit the said chamber, and a plunger-forming joint activator rod, disposed in the rest of the chamber with a proximal gripping part.

When a connection device such as that previously defined is combined, for example, with a syringe:

on the one hand, the distal end of the chamber-forming body is shaped according to the adapter defined in paragraph a) above of the preceding general definition, with the collar being connected or attached to this adapter, as defined in paragraph b) above of the preceding general definition, on the other hand, a needle assembly forming a connection device such as that defined in paragraph a) above of the preceding general definition, wherein the needle forms the axial passage in fluid communication with the interior of the said device.

In general, a syringe such as that previously defined is supplied to the user, e.g., medical personnel, in two parts, i.e.:

a first part consisting of the syringe strictly speaking, of glass or plastic material, discardable or reusable, prefilled or not;

and the needle assembly, such as defined previously, contained at least partially in a protective cover in order to prevent any accidental contact between the tip of the needle and the user; means disposed between the outside of the cap and the inside of the cover making it possible to wedge in the needle assembly so that it rotates in the cover, wherein these means may consist of longitudinal ribs cooperating with longitudinal slots;

in its proximal part, the cover may also comprise a collar-receiving retainer connected and attached to the adapter of the syringe.

These two components are handled as follows.

The user connects the cover retainer with the syringe collar and consequently the cap with the axial housing of the collar, doing so in such a manner as to achieve alignment along an axis common to the syringe with its collar, the needle assembly, and the protective cap.

By screwing the outer flange of the cap of the syringe assembly into the axial housing of the collar, a friction-activated connection is achieved between the internal distal seat of the cap and the external distal seat of the adapter; such a coupling cannot be split apart by pulling the needle assembly from the syringe strictly speaking, taking into account the fact that the collar and the cap are assembled by screwing.

After the screwing is completed and thus the friction-activated coupling has been achieved, it is possible, simply by pulling, to remove the protective cover.

The present invention has as its object to improve the previously defined Luer-lock, and more precisely to prevent any untimely disconnection under any circumstance, particularly when all or part of the connection device enters into contact with a liquid or oily material.

In accordance with the present invention, it has been discovered that when the proximal annular retention zone of the adapter and/or the proximal central retention opening of the collar comprise a circular band or cord coated by a roughening agent, it becomes difficult and even impossible to make the collar rotate around the adapter when the cap and the said collar have been screwed together on the one hand and to disengage the collar from the adapter when the protective cover is removed from the cap, on the other.

The present invention also comprises the following exemplified embodiments.

Preferably, the proximal annular retention zone of the adapter is a flat-bottomed groove, and the central retention opening of the collar forms a circular edge, adjusted to be locked into this groove; in this case, for example, the roughening agent coats the flat bottom of the groove and/or the edge of the central opening.

The roughening agent comprises particles of an inert and abrasive material, e.g., of ceramic, preferably encrusted and bound to the surface of the above-mentioned circular band.

The particles of inert and abrasive material are preferably bound by a binder coating the circular band.

The roughening agent, in the form of particles, can be deposited or supplied in the form of a circular band or cord, either in the proximal annular retention zone of the adapter or in the proximal central retention opening of the collar, by any appropriate means, such as sprinkling in the form of a powder, e.g., electrostatic dusting, brushing, etc.

However, preference will be given to any process consisting of forming a solution or suspension of the binder in an appropriate liquid medium, of coating the above-mentioned circular band with the binder and the particles of the roughening agent in suspension or solution, and then of eliminating the liquid medium. In this regard, and for all practical purposes, reference is made to the processes described in document U.S. Pat. No. 4,589,871.

The roughening agent can be applied to the surface of the band forming contact between the collar and the adapter according to any appropriate system, e.g., in a continuous manner, in strips, or by stippling.

The roughening agent may be a physical means making it possible to obtain the roughness sought on the circular band forming contact between the collar and the adapter. Such a physical means may consist of abrasion with an airflow under pressure carrying abrasive particles, or a laser beam.

The present invention is now described in reference to the attached drawing, in which:

FIG. 1 represents a Luer-lock type syringe, not connected to the needle assembly;

FIG. 2 represents the same syringe connected to a needle assembly, protected by a protective cover;

FIG. 3 represents the connection device strictly speaking, in axial view, before assembly;

FIG. 4 represents the same device, still in axial view, after connection has been accomplished between the needle and the collar on the one hand and the cap equipped with the axial passage or needle on the other.

The present invention is now described in reference to a syringe comprising in general:

A syringe 20 strictly speaking;

And a needle assembly 30, provided with a protective cover 31.

The syringe 20 traditionally comprises:

A body 21, manufactured of glass or a plastic material;

A sealant joint 22 forming a plunger, and with the rest of the body 21 delimiting a chamber 23 of varying volume for the liquid or fluid to be ejected or drawn;

A rod 24 disposed coaxially to the body 21, comprising a proximal handling end 24a, and a distal end 24b attached to the joint 22, e.g., by screwing.

The needle assembly 30 comprises:

A connection device 8, the distal part of which forms an arrangement 8a with longitudinal ribs 8b to accommodate rotational wedging;

A needle or axial passage 13 in one piece with the cap, in fluid communication with the inside of the said cap;

A protective cover 31, closed at its distal end 31a, producing an axial passage 31a for needle 13, and provided with longitudinal slots 31b respectively for the reception or insertion of ribs 8b; the cover also comprises a flared proximal part 31a.

The connection device 1 strictly speaking, accompanied on the one hand by the needle assembly 30 and on the other by the syringe 20 equipped with its collar 5, is described below.

This sealant connection device thus comprises:

a) An adapter 2 forming the axial end of body 21 of syringe 20, in which an internal axial passage 2a is provided; this adapter comprises an external distal seat 3 with sealant coupling, i.e., a friction-activated connection, e.g., of a frustoconical shape, and a proximal annular retention zone 4, consisting, for example, of a flat-bottomed groove 4a;

b) A collar 5, e.g., of injected plastic material, providing an open axial housing 5a; the wall 6 of this collar comprises a cylindrical distal part 6a with an internal threading 12, and a proximal part 6b in which a proximal central opening 7 is provided; this central retention opening forms a circular edge 7a, the diameter of which is adjusted to that of the proximal annular zone 4 of the adapter 2, which permits the collar 5 to be locked into the proximal annular retention zone 4 or flat-bottomed groove of adapter 2; thus, collar 5 is attached in a translational and/or rotational manner to adapter 2, by insertion between this annular zone 4 or groove and the central proximal opening 7, and more precisely the edge 7a of the collar 5;

c) A connection device 8 comprising another additional, internal junction seat 9, e.g., of a frustoconical shape, i.e., with coupling by friction, fitted to the external distal coupling seat 3 of adapter 2; this device also comprises two proximal and transverse external and radial flanges 10, together forming a thread 11 fitted to the internal threading 12 of the collar 5; and as indicated previously, the axial needle 13 is in fluid communication with the interior of the cap 8.

In accordance with the present invention, the proximal annular retention zone 4 of adapter 2, e.g., the flat-bottomed groove 4a, and/or the central retention opening 2 of the collar 5, or the circular edge 7a, comprise a circular band 4a coated with or treated by a roughening agent; preferably this roughening agent coats the flat bottom 4a of the groove, and/or the edge 7a of the central opening 7.

The operation of the connection device may be deduced from comparing the illustrations shown in FIGS. 3 and 4, and has been explained in the introductory part of the present description.

Thanks to the roughening agent, a complete and ensured connection of the needle assembly 30 to the adapter 2 of the syringe 20 is achieved.

Different variants of the solution according to the invention may be considered:

The proximal annular retention zone 4 of the adapter may be different from a groove; in the case of a groove, the latter may have a concave or angular base;

The roughening agent may consist of a system for grinding an originally smooth surface by abrasion or chemical attack, and may also consist of an adhesive applied by any appropriate means.

What is claimed is:

1. Connection device for medical use, of the Luer lock type, comprising:

a) An adapter (2) having an axial internal passage (2a), comprising a junction seat (3) and a proximal annular retention zone (4);

b) A collar (5) providing an axial open housing (5a) whose wall (6) contains a distal part (6a) with internal threading (12) and a transverse proximal part (6b) in which provision is made for a proximal central retention opening (7), whose diameter is adjusted to that of the said proximal annular zone (4) of the adapter (2), wherein the said collar (5) is attached in translational or rotational manner to the adapter (2), by insertion between the proximal annular retention zone (4) of the said adapter and the proximal central retention opening (7);

c) A connection device (8) comprising another additional junction seat (9), fitted to the junction seat (3) of the adapter (2), and at least one external proximal, transverse flange (10), forming a thread (11) fitted to the internal threading (12) of the collar (5), with an axial passage (13) in fluid communication with the interior of the said cap (8), characterized by the fact that one of the proximal annular retention zone (4) of the adapter (2) and the proximal central retention opening (7) of the collar (5) contain a circular band or cord (4a) coated or treated with a roughening agent, further characterized by the fact that the proximal annular retention zone (4) of the adapter (2) is a groove with a flat bottom (4a), and the central retention opening (7) of the collar (5) forms a circular edge (7a) fitted to lock into the said groove, and further characterized by the fact that the roughening agent coats the flat bottom (4*a*) of the groove and/or the edge (7*a*) of the central opening.

2. Connection device for medical use, of the Luer lock type, comprising:

an adapter (2) having an axial internal passage (2*a*), comprising a first junction seat (3) and a proximal annular retention zone (4);

a collar (5) providing an axial open housing (5*a*) whose wall (6) contains a distal part (6*a*) with internal threading (12) and a transverse proximal part (6*b*) in which provision is made for a proximal central retention opening (7), whose diameter is adjusted to that of the said proximal annular zone (4) of the adapter (2), wherein the said collar (5) is attached in translational or rotational manner to the adapter (2), by insertion between the proximal annular retention zone (4) of the said adapter and the proximal central retention opening (7);

a connection device (8) comprising a second junction seat (9), fitted to the first junction seat (3) of the adapter (2), and an external proximal, transverse flange (10), forming a thread (11) fitted to the internal threading (12) of the collar (5), with an axial passage (13) in fluid communication with the interior of the said can (8);

characterized by the fact that one of the proximal annular retention zone (4) of the adapter (2) and the proximal central retention opening (7) of the collar (5) contain a circular band or cord (4*a*) coated or treated with a roughening agent;

further characterized by the fact that the proximal annular retention zone (4) of the adapter (2) is a groove with a flat bottom (4*a*), and the central retention opening (7) of the collar (5) forms a circular edge (7*a*) fitted to lock into the said groove;

further characterized by the fact that the roughening agent coats the flat bottom (4*a*) of the groove and/or the edge (7*a*) of the central opening;

further characterized by the fact that the roughening agent comprises particles of an inert and abrasive material, preferably encrusted and bound to one of the surface of the circular band (4*a*) and the edge (7*a*).

3. Device according to claim 2, characterized by the fact that the particles of the inert and abrasive material are bound by a binder coating one of the circular band (4*a*) and the edge (7*a*).

4. Connection device for medical use, of the Luer lock type, comprising:

an adapter (2) having an axial internal passage (2*a*), comprising a first junction seat (3) and a proximal annular retention zone (4);

a collar (5) providing an axial open housing (5*a*) whose wall (6) contains a distal part (6*a*) with internal threading (12) and a transverse proximal part (6*b*) in which provision is made for a proximal central retention opening (7), whose diameter is adjusted to that of the said proximal annular zone (4) of the adapter (2), wherein the said collar (5) is attached in translational or rotational manner to the adapter (2), by insertion between the proximal annular retention zone (4) of the said adapter and the proximal central retention opening (7);

a connection device (8) comprising a second junction seat (9), fitted to the first junction seat (3) of the adapter (2), and an external proximal, transverse flange (10), forming a thread (11) fitted to the internal threading (12) of the collar (5), with an axial passage (13) in fluid communication with the interior of the said cap (8);

characterized by the fact that one of the proximal annular retention zone (4) of the adapter (2) and the proximal central retention opening (7) of the collar (5) contain a circular band or cord (4*a*) coated or treated with a roughening agent;

further characterized by the fact that the proximal annular retention zone (4) of the adapter (2) is a groove with a flat bottom (4*a*), and the central retention opening (7) of the collar (5) forms a circular edge (7*a*) fitted to lock into the said groove;

further characterized by the fact that the roughening agent coats the flat bottom (4*a*) of the groove and/or the edge (7*a*) of the central opening;

further characterized by the fact that the junction seat (3) has a frustoconical shape.

* * * * *